(12) United States Patent
Herrera et al.

(10) Patent No.: US 8,110,608 B2
(45) Date of Patent: Feb. 7, 2012

(54) SOLID FORM SODIUM LAURYL SULFATE (SLS) PESTICIDE COMPOSITION

(75) Inventors: Kelly Herrera, South St. Paul, MN (US); Stephen John Barcay, Burnsville, MN (US)

(73) Assignee: Ecolab USA Inc., St. Paul, MN (US)

( * ) Notice: Subject to any disclaimer, the term of this patent is extended or adjusted under 35 U.S.C. 154(b) by 426 days.

(21) Appl. No.: 12/477,640

(22) Filed: Jun. 3, 2009

(65) Prior Publication Data

US 2009/0306206 A1   Dec. 10, 2009

Related U.S. Application Data

(60) Provisional application No. 61/059,168, filed on Jun. 5, 2008.

(51) Int. Cl.
*A61K 31/10* (2006.01)
*A61N 41/10* (2006.01)

(52) U.S. Cl. ....................................................... 514/709
(58) Field of Classification Search .................... 514/709
See application file for complete search history.

(56) References Cited

U.S. PATENT DOCUMENTS

| | | | |
|---|---|---|---|
| 4,636,523 A | 1/1987 | Plummer | |
| 4,709,068 A | 11/1987 | Sieburth | |
| 4,737,509 A | 4/1988 | Plummer | |
| 4,808,762 A | 2/1989 | Meier et al. | |
| 5,300,503 A | 4/1994 | Peake et al. | |
| 5,521,192 A | 5/1996 | Henrie, II et al. | |
| 5,683,971 A | 11/1997 | Rose et al. | |
| 5,998,484 A | 12/1999 | Zobitne et al. | |
| 6,277,389 B1 | 8/2001 | Pullen | |
| 6,582,712 B2 | 6/2003 | Pullen | |
| 6,849,633 B2 | 2/2005 | Okui et al. | |
| 7,019,036 B2 | 3/2006 | Hiromoto | |
| 7,125,565 B2 | 10/2006 | Sugishita et al. | |
| 7,201,926 B2 | 4/2007 | Fried et al. | |
| 7,371,768 B2 | 5/2008 | Okui et al. | |
| 2003/0152603 A1* | 8/2003 | Johnson | 424/405 |
| 2005/0038094 A1 | 2/2005 | Warrington | |

FOREIGN PATENT DOCUMENTS

| | | |
|---|---|---|
| EP | 0008880 | 3/1980 |
| GB | 1572357 | 7/1980 |
| GB | 1604860 | 12/1981 |
| GB | 2144994 | 3/1985 |
| GB | 2145086 | 3/1985 |
| WO | 93/22915 | 11/1993 |

OTHER PUBLICATIONS

International Search Report and Written Opinion issued in PCT/IB2009/052400, mailed Feb. 3, 2010, 7 pages.

* cited by examiner

*Primary Examiner* — Johann Richter
*Assistant Examiner* — Thor Nielsen
(74) *Attorney, Agent, or Firm* — Faegre Baker Daniels LLP

(57) ABSTRACT

A pesticide composition and method of eliminating pests combines water and a solid form of sodium lauryl sulfate to form a pesticide composition effective to cause mortality in pests. The pesticide composition is applied to the indoor structure in an area which the pests inhabit. The sodium lauryl sulfate can be in needle form, pellet form or powder form and constitutes between about 1% and about 10% by weight of the pesticide composition. The pesticide composition may be applied to an area inhabited by cockroaches, including, but not limited to, in crevices, cracks, corners, wall and floor junctures or other enclosed or partially enclosed areas of a structure.

15 Claims, No Drawings

SOLID FORM SODIUM LAURYL SULFATE (SLS) PESTICIDE COMPOSITION

CROSS REFERENCE TO RELATED APPLICATIONS

This application claims the benefit under 35 U.S.C. §119 of U.S. Provisional Application No. 61/059,168, filed on Jun. 5, 2008, entitled "Solid Form Sodium Lauryl Sulfate (SLS) Pesticide Composition," which is herein incorporated by reference in its entirety.

TECHNICAL FIELD

The present invention relates generally to the field of pesticides. In particular, the present invention relates to using a solid form of sodium lauryl sulfate (SLS) in a pesticide composition. The present invention also relates to methods of using the pesticide composition.

BACKGROUND

Left unattended, pests such as insects and rodents can quickly infest enclosed structures, such as restaurants and homes. Examples of crawling pests which can infest areas in and around enclosed structures include, for example, cockroaches, ants, ground beetles and spiders. In addition to being a nuisance, some of these pests can also bring pathogens into the restaurant or home, creating unsanitary eating and living conditions.

The use of pesticide compositions has aided in decreasing the infestation of insects in and around residential and commercial structures. Various types of pesticide compositions and methods of repelling or terminating crawling pests are currently available, including gel baits, glue pads and poisons. Because the pests can enter walls through small cracks and crevices and inhabit relatively inaccessible areas, such as within floors and behind walls, various tools can be used to "flush" the pests from the wall. For example, flushing agents can be sprayed into the areas to irritate or agitate the pests and cause them to leave the inaccessible areas and come out into the open and expose themselves. Once the pests enter the open environment, they are exposed to a pesticide composition that terminates them.

In more recent years, attention has been directed to producing pesticides that are effective and ecologically friendly. In line with this trend, the Environmental Protection Agency (EPA) has issued a list of minimum risk pesticides §25(b) of the Federal Insecticide, Fungicide, and Rodenticide Act (FIFRA) that are not subject to federal registration requirements because their active and inert ingredients are demonstrably safe for their intended use. There is an ongoing need to provide effective pesticides which have reduced environmental impact.

SUMMARY

One embodiment of the present invention is a method of eliminating cockroaches by mixing water and solid needle form sodium lauryl sulfate to form a pesticide composition effective to cause mortality in cockroaches, wherein the sodium lauryl sulfate constitutes between about 1% and about 10% by weight of the pesticide composition, and applying the pesticide composition to an enclosed or partially enclosed area in a structure inhabited by cockroaches. The pesticide composition may be applied to an area inhabited by cockroaches, including, but not limited to, in crevices, cracks, corners, wall and floor junctures or other enclosed or partially enclosed areas of the indoor structure.

Another embodiment of the present invention is a pesticide composition produced by the method of combining water and solid needle form sodium lauryl sulfate to form a solution effective to cause mortality in pests. The concentration of sodium lauryl sulfate may be less than about 10% by weight of the pesticide composition, more particularly between about 1% and about 6% by weight of the pesticide composition. The pesticide composition according to certain embodiments may include only water and sodium lauryl sulfate, essentially only water and sodium lauryl sulfate, or may be free or substantially free of non-food grade components and/or components that are not ecologically safe.

DETAILED DESCRIPTION

The pesticide composition of the present invention may be employed at any of a wide variety of locations in which it is desired to eliminate pest infestation. The pesticide composition is effective in killing crawling pests, and in particular cockroaches. In addition, the pesticide composition is generally more ecologically sustainable than traditional pesticides, making it particularly useful where it is desired to use an environmentally friendly pesticide. Such applications include using the pesticide composition in and around restaurants, stores, homes, or other generally enclosed structures in which humans and animals are present. While the pesticide composition is discussed as being used to eliminate cockroaches, the pesticide composition may be used to eliminate any crawling pests, such as, for example, ants, ground beetles, spiders and the like. In addition, while the pesticide composition is discussed as being applied to and around partially enclosed or enclosed areas, the pesticide composition may also be used in an agricultural environment.

The pesticide compositions may include concentrate compositions or may be diluted to form use compositions. In general, a concentrate refers to a composition that is intended to be diluted with water to provide a use solution that contacts an object to provide the desired effect. The pesticide composition that contacts the pests or surrounding areas can be referred to as the use composition. The use solution can include additional functional ingredients. The use composition can have a solids content that is sufficient to provide the desired level of efficacy while avoiding wasting the pesticide composition. The solids concentration refers to the concentration of the non-water components in the use composition.

In one embodiment, the pesticide composition of the present invention includes a combination of sodium lauryl sulfate (SLS) and water. In particular, the pesticide composition includes a combination of a solid form of sodium lauryl sulfate and water. Suitable component concentrations for a concentrate of the pesticide composition include between about 90% and about 100% sodium lauryl sulfate by weight and balance water, particularly between about 93% and about 100% sodium lauryl sulfate by weight and balance water and more particularly between about 95% and about 100% sodium lauryl sulfate by weight and balance water. Suitable component concentrations for a use solution of the pesticide composition include between about 1% and about 10% sodium lauryl sulfate by weight and balance water and particularly between about 1% and about 6% sodium lauryl sulfate by weight and balance water. At concentrations higher than about 12% by weight sodium lauryl sulfate, solid form sodium lauryl sulfate may not effectively form a solution. In other embodiments, similar intermediate concentrate and use concentrations may also be present in the cleaning compositions of the invention.

Examples of suitable solid forms of sodium lauryl sulfate include, but are not limited to, powder, pellet and block forms. An example of a particularly suitable pellet form of sodium lauryl sulfate is needle form sodium lauryl sulfate. An example of a suitable commercially available needle form sodium lauryl sulfate includes Stepanol DX®, CAS number 151-21-3, available from Stephan Company, Northfield, Ill. While both powder form and pellet form sodium lauryl sulfate may be used to form the pesticide composition of the present invention, pellet form sodium lauryl sulfate is generally easier to handle and does not become airborne as easily as other solid forms.

When liquid concentrate form sodium lauryl sulfate is used, suitable component concentrations for the pesticide composition include between about 1% and about 18% sodium lauryl sulfate by volume and balance water and particularly between about 6% and about 18% sodium lauryl sulfate by volume and balance water. While the liquid concentrate form of sodium lauryl sulfate may also be effective in eliminating pests, liquid concentrate sodium lauryl sulfate has a freezing point of about 53 degrees Fahrenheit, making liquid concentrate sodium lauryl sulfate difficult to use effectively in certain applications.

Because sodium lauryl sulfate is on the §25(b) exempt list of minimum risk pesticides published by the EPA in the FIFRA, the pesticide composition of the present invention is not only ecologically acceptable but is also a food grade material. In one embodiment, the pesticide composition includes an effective amount of sodium lauryl sulfate and water. In another embodiment, the pesticide composition further includes additional components that are on the list of minimum risk pesticides and/or materials that are otherwise considered ecologically safe, non-toxic or food grade. For example, in one embodiment, the pesticide composition does not include components which may be considered toxic or carcinogenic when exposed to humans. In a further embodiment, the pesticide composition contains conventional pesticides or other components in concentrations of less than about 0.5% by weight of a use solution of the pesticide composition, particularly less than about 0.1% by weight of a use solution of the pesticide composition and more particularly less than about 0.01% by weight of a use solution of the pesticide composition. In yet another embodiment, the pesticide composition includes conventional pesticides at lower concentrations than typically required when used as the primary pesticide due to the presence of the sodium lauryl sulfate.

Additional Functional Ingredients

In a further embodiment, the pesticide composition may also include additional components or agents, such as additional functional ingredients. As such, in some embodiments, the pesticide composition including sodium lauryl sulfate and water may provide a large amount, or even all of the total weight of the pesticide composition, for example, in embodiments having few or no additional functional materials disposed therein. The functional materials provide desired properties and functionalities to the pesticide composition. For the purpose of this application, the term "functional materials" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and a broad variety of other functional materials may be used.

The pesticide composition of the present invention may include attractants such as cockroach pheromones (e.g., sex attractants, aggregation pheromones) or food-based attractants (e.g, methylcyclopentenalone, maltol, fenugreek and other flavorings). When an attractant is included in the pesticide composition, the attractant may constitute between about 0.1% and about 5% by weight of a use solution of the pesticide composition.

The pesticide composition may also optionally include humectants such as glycerol to slow evaporation and maintain wetness of the pesticide composition after application. When a humectant is included in the pesticide composition, the humectant may constitute between about 0.5% and about 10% by weight of the pesticide composition.

The pesticide composition may also optionally include a foaming agent. When a foaming agent is included in the pesticide composition, the foaming agent may constitute between about 1% and about 10% by weight of the pesticide composition.

Packaging

The pesticide composition may be packaged by any conventional means known in the art. For example, solid form sodium lauryl sulfate and other functional ingredients may be premixed and packaged as a concentrate in a bucket. Alternatively, the pesticide composition may be packaged in a water-soluble sachet for easy disposal after use and reduced packaging waste.

Methods of Use

In general, a pesticide composition of the present invention using a solid form of sodium lauryl sulfate can be created by combining a solid form of sodium lauryl sulfate, water, and any additional functional components and allowing the components to interact. In a first embodiment, the pesticide composition may include needle form sodium lauryl sulfate and water. In an exemplary embodiment, a use solution of the pesticide composition includes between about 1% and about 10% by weight of a solid form of sodium lauryl sulfate and balance water.

In a second embodiment, the pesticide composition may include a solid form of sodium lauryl sulfate, water, attractant, humectant and foaming agent. In an exemplary embodiment, a use solution of the pesticide composition includes between about 1% and about 10% by weight active solid form sodium lauryl sulfate, between about 0.1% and about 5% by weight attractant, between about 0.5% and about 10% by weight humectant, between about 1% and about 10% by weight foaming agent and balance water.

The concentrate may be diluted with water at the location of use to provide the use solution. Once the pesticide composition has been thoroughly mixed to form a substantially homogeneous solution, the pesticide composition may be applied onto a surface as a spray or foam. The use solution is applied onto the surface for an amount of time sufficient to terminate the pests. The pesticide composition can be applied in and around areas such as apartment buildings, bakeries, beverage plants, bottling facilities, breweries, cafeterias, candy plants, canneries, cereal processing and manufacturing plants, cruise ships, dairy barns, poultry facilities, flour mills, food processing plants, frozen food plants, homes hospitals, hotels, houses, industrial buildings, kennels, kitchens, laboratories, manufacturing facilities, mausoleums, meat processing and packaging plants, meat and vegetable canneries, motels, nursing homes, office buildings, organic facilities, restaurants, schools, stores, supermarkets, warehouses and other public buildings and similar structures. In particular, the pesticide composition can be applied to surfaces, such as floors, where pests may harbor, including cracks, crevices, niches, dark areas, drains, and other harborage sites.

EXAMPLES

The present invention is more particularly described in the following examples that are intended as illustrations only, since numerous modifications and variations within the scope of the present invention will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques.

Panel Exposure Test 6 inch by 6 inch stainless steel panels were sprayed with a test sample. Ten adult male cockroaches were placed onto the wet panels for about 1 minute. A 6 inch diameter greased PLEXIGLASS® ring was used to ensure that the insects remained on the panel for the desired amount of time. Once the cockroaches were removed, the cockroaches were transferred to pre-greased jars for observation of mortality data. During the data collection period, the cockroaches were provided with food and water. Mortality was tracked at 1, 2, 4, 24 and 48 hours post-exposure. This test was performed 6 times.

Examples 1, 2 and 3 and Comparative Examples A, B and C

The compositions of Examples 1, 2 and 3 are compositions of the present invention using needle form sodium lauryl sulfate (SLS) as the active ingredient in a pesticide composition. The compositions of Examples 1, 2 and 3 were mixed with water to form, respectively, about 1 wt %, about 3 wt % and about 6 wt % solutions. To obtain the 3 wt % and 6 wt % solutions, heat was applied to the SLS and water combination until the SLS went into solution. The heat was applied using a microwave.

The compositions of Examples A, B and C are comparative compositions of the present invention using powder form SLS combined with water to form, respectively, about 1 wt %, about 3 wt % and about 6 wt % solutions. The compositions of Comparative D, E and F are comparative compositions using liquid form SLS combined with water to form, respectively, about 6 wt %, about 12 wt % and about 18 wt % solutions.

All forms of the sodium lauryl sulfate are commercially available from Stephan Company located in Northfield, Ill.

The various pesticide compositions were applied onto stainless steel panels as described in the panel exposure test method described above. For the compositions of Examples 1, 2 and 3 and Comparative Examples A, B, C and E, each of the tests was run a total of 6 times, with a total of 60 test cockroaches. For the compositions of Comparative Examples D and F, tests were performed less than 6 times and the mortality data was multiplied by the appropriate factor to obtain a comparable set of data. Table 1 provides the percent solution for the compositions of Examples 1, 2 and 3 and Comparative Examples A, B, C, D, E and F and the percent cockroach mortality after 48 hours.

TABLE 1

| | | Mortality | | | | | |
|---|---|---|---|---|---|---|---|
| | | 1 Hour | 2 Hours | 4 Hours | 24 Hours | 48 Hours | % mortality at 48 hours |
| Example 1 | Needle Form 1% | 1/60 | 1/60 | 1/60 | 1/60 | 5/60 | 8.33% |
| Example 2 | Needle Form 3% | 6/60 | 6/60 | 6/60 | 6/60 | 6/60 | 10% |
| Example 3 | Needle Form 6% | 15/60 | 15/60 | 15/60 | 16/60 | 18/60 | 30% |
| Comp. Ex. A | Powder Form 1% | 0/60 | 0/60 | 0/60 | 0/60 | 1/60 | 1.67% |
| Comp. Ex. B | Powder Form 3% | 5/60 | 5/60 | 5/60 | 5/60 | 7/60 | 11.67% |
| Comp. Ex. C | Powder Form 6% | 5/60 | 3/60 | 3/60 | 4/60 | 4/60 | 6.67% |
| Comp. Ex. D | Liquid Form 6% | 0/30 (0/60) | 0/30 (0/60) | 0/30 (0/60) | 1/30 (2/60) | 3/30 (6/60) | 10% |
| Comp. Ex. E | Liquid Form 12% | 0/60 | 0/60 | 0/60 | 0/60 | 1/60 | 1.67% |
| Comp. Ex. F | Liquid Form 18% | 1/30 (2/60) | 1/30 (2/60) | 1/30 (2/60) | 1/30 (2/60) | 1/30 (2/60) | 3.33% |

As illustrated in Table 1, the needle form SLS in the compositions of Examples 1, 2 and 3 resulted in generally higher rates of mortality than the powder form SLS in the compositions of Comparative Examples A, B and C and the liquid form SLS in the compositions of Comparative Examples D, E and F. In particular, with a 1% solution, the composition of Example 1 killed about 6.67% of the cockroaches over 48 hours while the composition of Comparative Example A killed about 1.67% of the cockroach over the same period of time. With a 3% solution, the composition of Example 2 killed about 10% of the cockroaches over 48 hours while the composition of Comparative Example B killed about 11.67% of the cockroaches over the same period of time. With a 6% solution, the composition of Example 3 killed about 30% of the cockroaches over 48 hours. By comparison, the compositions of Comparative Example C and Comparative Example D killed about 6.67% and about 10% of the cockroaches, respectively, over the same period of time.

Because needle form and powder form SLS would not go into solution at 12% and 18%, only liquid SLS was tested. Even with a 12% solution and 18% solution, the compositions of Comparative Example E killed only 1 cockroach and Comparative Example F only killed 2 cockroaches. Thus, the mortality rate of a 12% and 18% solution of liquid SLS was lower than the mortality rate of a 1% solution of the needle form SLS.

The only difference in the compositions of Examples 1, 2 and 3, the compositions of Comparative Examples A, B and C and the compositions of Comparative Examples D, E and F was the form of SLS used. The results in Table 1 thus illustrates that compositions including needle form SLS and powder form SLS were the more effective in killing cockroaches than compositions including liquid form SLS.

Examples 4, 5, 6, 7, 8, 9, 10, 11 and 12

After determining that needle form SLS was more efficient at killing cockroaches than either liquid form or powder form SLS, testing on the method of application of the SLS was performed. This included the amount of SLS applied onto the panels. The compositions of Examples 4, 5, 6, 7, 8, 9, 10, 11 and 12 are compositions of the present invention using needle form sodium lauryl sulfate (SLS) as the active ingredient in a pesticide composition. Each of Examples 4, 5, 6, 7, 8, 9, 10, 11 and 12 were mixed with water to form 1% solutions and applied onto the panels as described above. Example 4 applied about 0.74 grams of the pesticide composition, Example 5 applied about 0.89 grams of the pesticide composition, Example 6 applied about 1.12 grams of the pesticide composition, Example 7 applied about 1.55 grams of the pesticide composition, Example 8 applied about 2.11 grams of the pesticide composition, Example 9 applied about 2.12 grams of the pesticide composition, Example 10 applied about 2.65 grams of the pesticide composition, Example 11 applied about 2.92 grams of the pesticide composition and Example 12 applied about 4.92 grams of the pesticide composition.

Table 2 provides the grams of pesticide composition applied for Examples 4, 5, 6, 7, 8, 9, 10, 11 and 12 and the percent cockroach mortality after 48 hours.

TABLE 2

| | | Mortality | | | | | % mortality at 48 hours |
|---|---|---|---|---|---|---|---|
| | | 1 Hour | 2 Hours | 4 Hours | 24 Hours | 48 Hours | |
| Example 4 | 0.74 grams | 5/80 | 7/80 | 6/80 | 7/80 | 7/80 | 8.75 |
| Example 5 | 0.89 grams | 66/80 | 69/80 | 74/80 | 67/80 | 67/80 | 83.75 |
| Example 6 | 1.12 grams | 29/80 | 28/80 | 33/80 | 30/80 | 31/80 | 38.75 |
| Example 7 | 1.55 grams | 48/80 | 48/80 | 46/80 | 48/80 | 48/80 | 60.00 |
| Example 8 | 2.11 grams | 70/80 | 71/80 | 69/80 | 67/80 | 68/80 | 85.00 |
| Example 9 | 2.12 grams | 64/80 | 69/80 | 59/80 | 62/80 | 62/80 | 77.5 |
| Example 10 | 2.65 grams | 62/80 | 64/80 | 69/80 | 67/80 | 67/80 | 83.75 |
| Example 11 | 2.92 grams | 77/80 | 78/80 | 76/80 | 76/80 | 76/80 | 95.00 |
| Example 12 | 4.92 grams | 77/80 | 77/80 | 76/80 | 77/80 | 77/80 | 96.25 |

As illustrated in Table 2, as the amount of needle form SLS applied onto the panels increased, the rate of cockroach mortality also increased. When the amount of needle form SLS applied onto the panels nearly doubled from about 0.74 grams (Example 4) to about 1.55 grams (Example 7), the percent mortality of cockroaches at 48 hours increased by about 85.42%. When the amount of needle form SLS applied onto the panels nearly doubled again from about 1.55 grams (Example 7) to about 2.92 grams (Example 11), the percent mortality of cockroaches at 48 hours increased by another about 36.84%. When the amount of needle form SLS applied onto the panels nearly doubled again from about 2.92 grams (Example 11) to about 4.92 grams (Example 12), the percent mortality of cockroaches at 48 hours increased by another about 1.3%. In all, as the amount of needle form SLS applied onto the panels increased from about 0.74 grams (Example 4) to about 4.92 grams (Example 12), the percent mortality of cockroaches at 48 hours increased by over 90%, from 8.75% to 96.25%.

Table 2 thus shows that the efficacy of sodium lauryl sulfate, and particularly needle form SLS, is related to the amount of SLS applied onto the surface of the panel.

Jar Exposure Test

The test samples were sprayed directly onto ten cockroaches that were placed into greased, 16 ounce jars. The jars were agitated to ensure that all of the cockroaches in the jar came into contact with the test sample. The cockroaches stayed in the treated jars for observation of mortality data. During the data collection period, the cockroaches were provided with food and water. Mortality was tracked at 1, 2, 4, 24 and 48 hours post-exposure. This test was performed 6 times. Generally, a cockroach mortality of about 70% or higher is considered acceptable. A cockroach mortality of about 90% or higher is considered excellent.

Examples 13, 14 and 15 and Comparative Examples G, H, I, J, K, L and M

The compositions of Examples 13, 14 and 15 are compositions of the present invention using needle form sodium lauryl sulfate (SLS) as the active ingredient in a pesticide composition. The compositions were mixed with water to form about 1 wt %, about 3 wt % and about 6 wt % solutions, respectively.

The compositions of Comparative Examples G, H and I are comparative compositions of the present invention using powder form SLS. The compositions were mixed with water to form about 1 wt %, about 3 wt % and about 6 wt % solutions, respectively. The compositions of Comparative Examples J, K, L and M are also comparative compositions using liquid form SLS. The compositions were mixed with water to form about 6 wt %, about 12 wt % and about 18 wt % solutions, respectively.

The various exemplary compositions were sprayed into jars as described in the test method above. For the compositions of Examples 13, 14, and 15 and Comparative Examples G, H, I and J, each of the tests were run a total of 6 times, with a total of 60 test cockroaches. For the compositions of Comparative Examples K, L and M, tests were performed less than 6 times and the mortality data was multiplied by the appropriate factor to obtain a comparable set of data. Table 3 provides the percent solution for the compositions of Examples 13, 14 and 15 and the compositions of Comparative Examples G, H, I, J, K, L and M and the percent of cockroach mortality after 48 hours.

TABLE 3

| | | Mortality | | | | | |
|---|---|---|---|---|---|---|---|
| | | 1 Hour | 2 Hours | 4 Hours | 24 Hours | 48 Hours | % mortality at 48 hours |
| Example 13 | Needle Form 1% | 53/60 | 53/60 | 53/60 | 53/60 | 55/60 | 91.7% |
| Example 14 | Needle Form 3% | 52/60 | 52/60 | 52/60 | 53/60 | 53/60 | 88.33% |
| Example 15 | Needle Form 6% | 53/60 | 53/60 | 53/60 | 53/60 | 56/60 | 93.33% |
| Comp. Ex. G | Powder Form 1% | 6/60 | 7/60 | 6/60 | 7/60 | 7/60 | 11.67% |
| Comp. Ex. H | Powder Form 3% | 28/60 | 27/60 | 27/60 | 25/60 | 28/60 | 46.67% |
| Comp. Ex. I | Powder Form 6% | 26/60 | 27/60 | 26/60 | 27/60 | 32/60 | 53.33% |
| Comp. Ex. J | Liquid Form 1% | 3/10 (18/60) | 4/10 (24/60) | 4/10 (24/60) | 4/10 (24/60) | 8/10 (48/60) | 80% |
| Comp. Ex. K | Liquid Form 6% | 12/30 (24/60) | 11/30 (22/60) | 10/30 (20/60) | 9/30 (18/60) | 10/30 (20/60) | 33.33% |
| Comp. Ex. L | Liquid Form 12% | 30/60 | 25/60 | 31/60 | 31/60 | 33/60 | 55% |
| Comp. Ex. M | Liquid Form 18% | 12/20 (36/60) | 11/20 (33/60) | 11/20 (33/60) | 11/20 (33/60) | 12/20 (36/60) | 60% |

As illustrated in Table 3, the needle form SLS in the compositions of Examples 13, 14 and 15 resulted in higher rates of mortality than the powder form SLS in the compositions of Comparative Examples G, H and I and the liquid form SLS in the compositions of Comparative Examples J, K, L and M. In particular, with a 1% solution, the composition of Example 13 killed about 91.7% of the cockroaches over 48 hours while the compositions of Comparative Example G and Comparative Example J killed about 11.67% and about 80% of the cockroaches, respectively, over the same period of time. With a 3% solution, the composition of Example 14 killed about 88.33% of the cockroaches over 48 hours while the composition of Comparative Example H killed about 46.67% of the cockroaches over the same period of time. With a 6% solution, the composition of Example 15 killed about 93.33% of the cockroaches over 48 hours. By comparison, the compositions of Comparative Example I and Comparative Example K killed about 53.33% and about 33.33% of the cockroaches, respectively, over the same period of time.

Because needle form and powder form SLS would not go into solution at 12% and 18%, only the liquid SLS was tested. Even with a 12% solution and 18% solution, the compositions of Comparatives Example L and M only killed about 55% and about 60% of the cockroaches, respectively. Thus, the mortality rate of 12% and 18% solutions including liquid SLS was lower than the mortality rate of a 1% solution including needle form SLS.

The only difference among the compositions of Examples 13, 14 and 15, the compositions of Comparative Examples G, H and I and the compositions of Comparative Examples J, K, L and M was the form of SLS used. The results in Table 3 illustrate that compositions including needle form SLS were more effective in killing cockroaches than compositions including powder and liquid form SLS. Pesticide compositions including solid form SLS may be effective at killing cockroaches, but would need to be applied at higher concentrations than pesticide compositions including powder form SLS.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention The following is claimed:

1. A method of eliminating crawling pests comprising:
   (a) mixing water and a solid needle form of sodium lauryl sulfate to form a pesticide composition use solution effective in causing mortality in crawling pests, wherein the sodium lauryl sulfate constitutes between about 1% and about 10% by weight of the pesticide composition; and
   (b) applying the pesticide composition to an enclosed or partially enclosed area in a structure inhabited by crawling pests.

2. The method of claim 1, wherein the sodium lauryl sulfate constitutes between about 1% and about 6% by weight of the pesticide composition.

3. The method of claim 1, wherein applying the pesticide composition comprises spraying the pesticide composition.

4. The method of claim 1, wherein applying the pesticide composition comprises allowing the pesticide composition to remain in the structure for at least about one hour.

5. The method of claim 4, wherein applying the pesticide composition comprises allowing the pesticide composition to remain in the structure for at least about twenty-four hours.

6. The method of claim 4, wherein applying the pesticide composition comprises allowing the pesticide composition to remain in the structure for at least about forty-eight hours.

7. The method of claim 1, wherein the pesticide composition further comprises at least one of: a pheromone, a food attractant, a humectant and a foaming agent.

8. The method of claim 1, wherein the crawling pests are cockroaches.

9. A method of eliminating cockroaches comprising:
(a) mixing water and needle form sodium lauryl sulfate to form a pesticide composition use solution effective to cause mortality in cockroaches, wherein the sodium lauryl sulfate constitutes between about 1% and about 10% by weight of the pesticide composition; and
(b) applying the pesticide composition to an enclosed or partially enclosed area in a structure inhabited by cockroaches.

10. The method of claim 9, wherein the sodium lauryl sulfate constitutes between about 1% and about 6% by weight of the pesticide composition.

11. The method of claim 9, wherein the pesticide composition further comprises at least one of: a pheromone, a food attractant, a humectant and a foaming agent.

12. The method of claim 9, wherein applying the pesticide composition comprises spraying the pesticide composition.

13. The method of claim 9, wherein applying the pesticide composition comprises allowing the pesticide composition to remain in the structure for at least about one hour.

14. The method of claim 13, wherein applying the pesticide composition comprises allowing the pesticide composition to remain in the structure for at least about twenty-four hours.

15. The method of claim 13, wherein applying the pesticide composition comprises allowing the pesticide composition to remain in the structure for at least about forty-eight hours.

* * * * *